United States Patent [19]

Kelsey

[11] Patent Number: 4,774,344

[45] Date of Patent: Sep. 27, 1988

[54] 2,2-BIS-PHENOL DIOXOLANES MONOMERS

[75] Inventor: Donald R. Kelsey, Hillsborough, N.J.

[73] Assignee: Amoco Corporation, Chicago, Ill.

[21] Appl. No.: 70,983

[22] Filed: Jul. 8, 1987

Related U.S. Application Data

[63] Continuation of Ser. No. 827,498, Feb. 3, 1986, abandoned, which is a continuation of Ser. No. 430,358, Sep. 30, 1982, abandoned.

[51] Int. Cl.$^4$ .................. C07D 317/20; C07D 317/24
[52] U.S. Cl. ..................................... 549/453; 549/454; 549/375; 549/374; 568/592
[58] Field of Search ................................ 549/453, 454

[56] References Cited

U.S. PATENT DOCUMENTS

| | | | |
|---|---|---|---|
| 3,734,888 | 5/1973 | Darms et al. | 525/419 |
| 3,948,946 | 4/1976 | Hofer et al. | 549/453 |
| 4,008,327 | 2/1977 | Kathawala | 549/453 |

OTHER PUBLICATIONS

Sulzbacher et al., JACS, 70, 2827 (1948).

*Primary Examiner*—Nicky Chan
*Attorney, Agent, or Firm*—Donald M. Papuga; William H. Magidson; Ralph C. Medhurst

[57] ABSTRACT

Described herein are novel monomers, polyketals derived from such monomer, improved process for the production of such monomers and a process for producing the polyketals.

6 Claims, No Drawings

2,2-BIS-PHENOL DIOXOLANES MONOMERS

This is a continuation of application Ser. No. 827,498, filed Feb. 3, 1986, which is a continuation of application Ser. No. 430,358, filed Sept. 30, 1982, both now abandoned.

BACKGROUND OF THE INVENTION

Bisphenols are used for the preparation of a variety of useful polymeric materials, including epoxy resins, polyesters, polycarbonates, and especially polyarylethers as described in, for example, U.S. Pat. No. 4,175,175. However, the ketal bisphenols of this invention are novel compounds.

The formation of the ketal moiety in a number of diverse organic compounds is well known in the art. The processes for the preparation of ketals and their corresponding heteroatom analogues, such as hemithioketals, can be accomplished by a number of synthetic methods. Examples of such methods have been reviewed, for example, in the following: H. J. Lowenthal in "Protective Groups in Organic Chemistry," J. F. W McOmie, ed., Plenum Press, 1973, p. 323ff; S. R. Sandler et al., "Organic Functional Group Preparations," Vol. 3, Academic Press, 1972, p. 2ff; C. A. Buehler et al., "Survey of Organic Synthesis," Wiley-Interscience, 1970, p. 513ff and vol. 2, 1977, p. 461ff; R. T. Bergstrom in "The Chemistry of Ethers, Crown Ethers, Hydroxyl Groups and Their Sulfur Analogues," Suppl. E, Part 2, S. Patai, ed., Wiley, 1980, p. 881ff; and F. A. J. Meskens, *Synthesis,* 501(1981).

Commonly, the ketal group is formed by reacting the corresponding carbonyl group with an alcohol or an alcohol derivative such as an orthoester, generally in the presence of an acid catalyst. It is also advantageous to conduct the reaction under conditions so as to remove the water of reaction and by-products, as for example, by distillation, by employing azeotropic solvents, as described in, for example M. Sulzbacher et al, *J. Amer. Chem. Soc.,* 70, 2827 (1948), by using drying agents, or by adding chemical agents such as trialkyl orthoesters or tetraalkyl orthosilicates.

The use of clay catalysts to prepare ketals is known in the art as taught by Thuy et al., (*Bull Soc. Chim. France,* 2558 (1975)) and by Taylor et al., (*Synthesis,* 467 (1977)) both of which employed montmorillonite clay catalysts. However in the case of the heretofore unknown ketal bisphenol monomers of this invention, improved processes for the efficient preparation of said monomers are highly desirable.

U.S. Pat. No. 3,734,888 is directed to polyketals and a process for their preparation. The polyketals are described in this patent as containing groups of the formula:

wherein the R is hydrogen or alkyl of 1 to 3 carbon atoms and n is 2 or 3. The polyketals are prepared by reacting an aromatic polyketone and a diol of the formula HO—(CR$_2$)$_n$—OH in the presence of an acid catalyst. The polyketals in the reference are described as soluble in solvents, and solutions of the polyketals in such solvents are useful as coating lacquers for metal conductors in wire or sheet form, for various plastic films, such as polyamides and polyesters and as adhesives. Additionally, the polyketals are described as useful in film or powder form as adhesives in thermally bonding metals and plastics when melt pressed to such materials.

DESCRIPTION OF THE INVENTION

Described herein are novel monomers, polyketals derived from such novel monomers, improved processes for the production of said monomers and a process for producing the polyketals.

The monomers of this invention have not been previously described in the literature nor have they have been used to prepare polymers, i.e. polyketals as herein defined.

Although methods known in the art may be applicable to the preparation of the ketal monomers of this invention, improved processes are necessary and desirable for the preparation of said ketal monomers and especially, for the preparation of the ketals derived from glycols and diaromatic ketones having one or more hydroxyl groups situated ortho or para to the carbonyl.

It has been discovered that the reaction of a glycol, an orthoester, and a solid catalyst, such as clay, with a diaromatic ketone produces the corresponding glycol ketal in improved yields and reaction times.

Furthermore, as compared to the process described in U.S. Pat. No. 3,734,888, supra, wherein preformed aromatic polyketones are converted to the corresponding polyketals under acid conditions, the process of this invention allows the preparation of polyketals from novel monomers under basic conditions.

The novel monomers of this invention are of the following formulae:

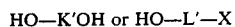

wherein K' is the residue of a substituted or unsubstituted aromatic or heteroaromatic nucleus containing from about 10 to about 40 carbon atoms and also containing at least one backbone difunctional unit of the following formula:

said unit stable to the basic polymerization conditions employed, wherein G and G' are selected from the group consisting of halide, —OR, —OCOR$^1$, —NR$^2$R$^3$, —NHCOR$^4$, —SR$^5$, wherein R and R$^1$-R$^5$ are each independently alkyl, aryl, or arylalkyl of from 1 to about 20 carbon atoms; R and R$^1$-R$^5$ may be substituted or unsubstituted, may contain heteroatoms, and may also be connected by a chemical bond thus connecting G and G', with the proviso that the R's should not contain functionality which is base sensitive such as hydroxyl; L' is the residue of a substituted or unsubstituted aromatic or heteroaromatic nucleus of from about 10 to about 40 carbon atoms containing at least one electron-withdrawing group situated ortho of para to X and also containing at least one difunctional backbone unit —C(G)(G')— as defined above and wherein X is a group displaced during the polymerization reaction.

Preferred and most preferred monomers are described below.

The polyketal is derived from the following:

(a) one or more monomers X-Z-Y, where Z is the residue of a substituted or unsubstituted aromatic or heteroaromatic nucleus of from about 5 to about 30 carbon atoms containing at least one electron-withdrawing group ortho or para to X and Y, wherein X and Y are groups displaced during the polymerization reaction;

(b) optionally one or more bisphenols HO-W-OH, where W is the residue of a substituted or unsubstituted aromatic or heteroaromatic nucleus of from about 5 to about 30 carbon atoms, and (c) one or more bisphenols HO—K'—OH, wherein K' is as defined above containing the unit —C(G)(G')— wherein G and G' are defined as above and also G and G' are also combined and wherein G and G' are combined and selected from the group consisting of $=$N—N—Ar, $=$NOH, $=$N—Ar and $=$N—NHCONR$^6$R$^7$, wherein Ar and Ar' are substituted or unsubstituted aryl of from about 5 to about 12 carbon atoms and R$^6$ and R$^7$ are hydrogen or as defined for R$^{1\text{-}5}$ above.

Preferably the polyketal is derived from the following:

(a) one or more monomers X-Z-Y where Z is

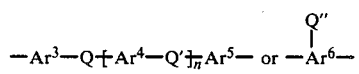

where Ar$^{3\text{-}6}$ are substituted or unsubstituted aryl radicals of from about 5 to about 18 carbon atoms, n is 0 to about 3, Q and Q' are electron withdrawing groups ortho or para to X and Y, and selected from the group consisting of —SO$_2$—, —CO—, —SO—, —N$=$N—, —C$=$N—, —C$=$N(O)—, imide, vinylene (—C$=$C—) and substituted vinylene such as —CF$_2=$CF$_2$— or —C$=$C(CN)—, perfluoroalkyl such as —CF$_2$—CF$_2$—, —P(O)R$^8$—, wherein R$^8$ is a hydrocarbon group, ethylidine (C$=$CH$_2$), C$=$CF$_2$, C$=$CCl$_2$, and the like and Q'' is an electron withdrawing group ortho or para to X and Y and selected from the group consisting of —NO$_2$, —CN, perfluoroalkyl such as —CF$_3$, —NO, —SO$_m$R$^8$ (m is 1 or 2), or hetero nitrogen as in pyridine and the like; and wherein the displaceable leaving groups X and Y are halogen, such as —F and —Cl, —NO$_2$, —OSOR$^8$, —OSO$_2$R$^8$, and the like;

(b) optionally one or more bisphenols HO—W—OH, where W is selected from the following:

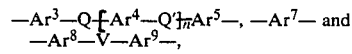

where n, Ar$^{3\text{-}5}$, Q, and Q' are as defined above, Ar$^{7\text{-}9}$ are as defined for Ar$^{3\text{-}5}$, and wherein V is a single bond, —O—, —S—, —S—S— or a difunctional hydrocarbon radical of from 1 to about 20 carbon atoms, such as alkyl, aryl, and alkylaryl radicals and rings fused to both Ar$^8$ and Ar$^9$;

(c) one or more bisphenol monomers HO—K'—OH where K' is selected from

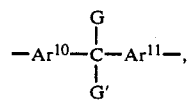

and —Ar$^3$—Q$^3$—[Ar$^4$—Q$^4$]$_{\bar{p}}$Ar$^5$— where G, G', and Ar$^{3\text{-}5}$ are as defined above, p is an integer of 1 to about 5, Q$^3$ and Q$^4$ are as defined for Q, Q', and V, with the proviso that at least one Q$^3$ and Q$^4$ is the group —C(G)(G')—, and Ar$^{10}$ and Ar$^{11}$ are substituted or unsubstituted aryl of from about 5 to about 18 carbon atoms such as phenylene, biphenylene, and —Ar$^8$—V—Ar$^9$— are as defined above.

Most preferably, the polyketal is derived from the following:

(a) one or more monomers X-Z-Y, where Z is selected from the following:

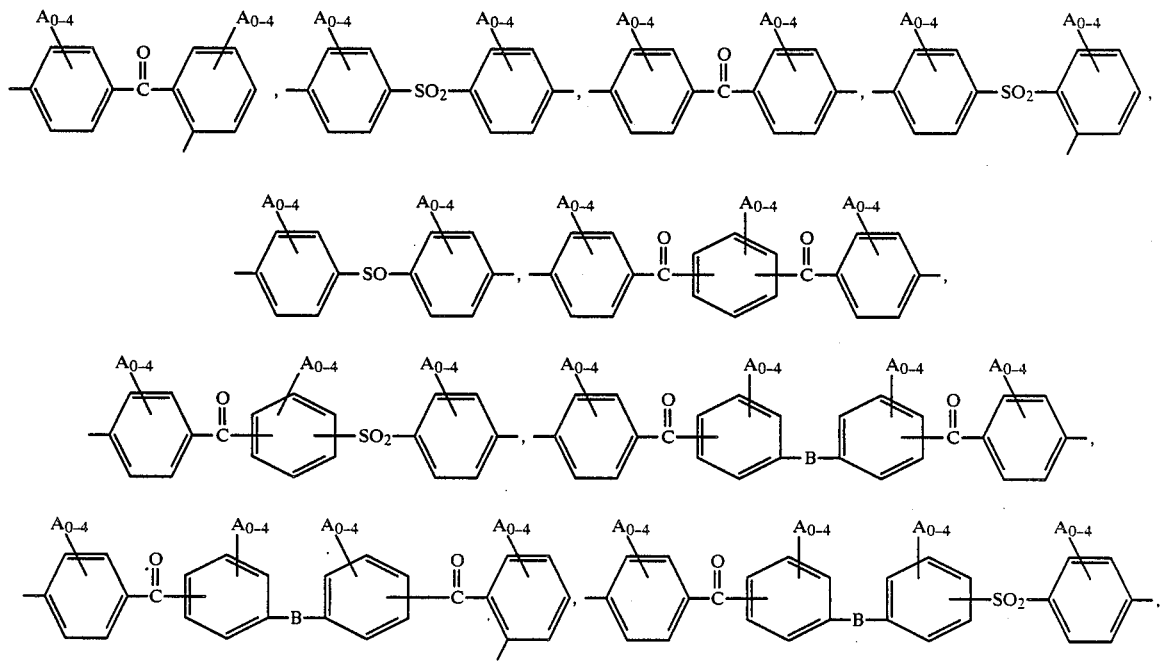

-continued

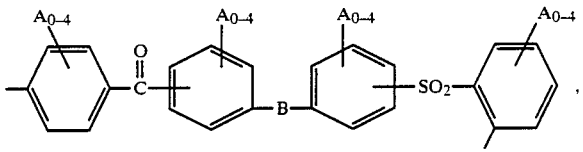

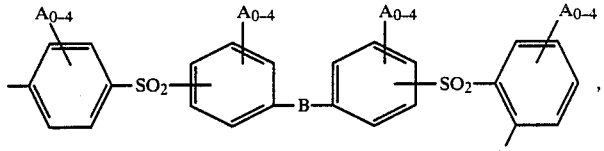

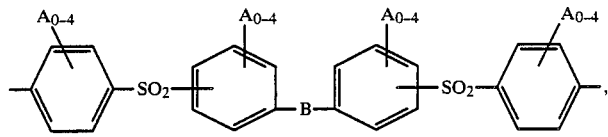

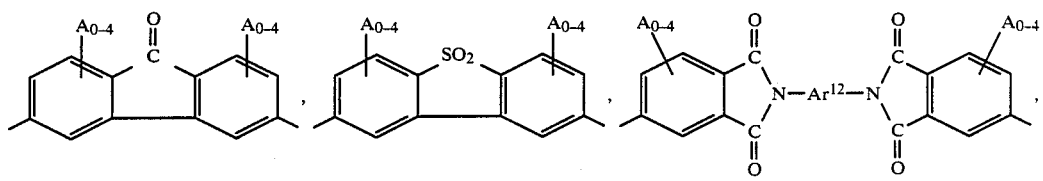

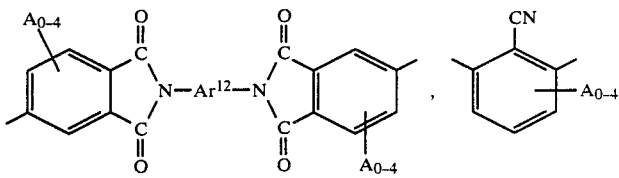

and isomers thereof, and wherein B is defined as above for V, Q, and Q', $Ar^{12}$ is defined as above for $Ar^{1-11}$, and A is a non-interfering substituent group unreactive under the polymerization conditions and independently selected from the group of common organic substituents such as hydrogen, alkyl, aryl, halogen, cyano, and the like, and wherein X and Y are halogen or nitro; and most preferably Z is

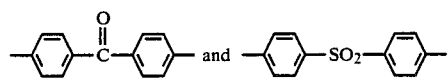

wherein X and Y are F or Cl and A is hydrogen;

(b) optionally one or more comonomer bisphenols HO—W—OH, where W is selected from the following:

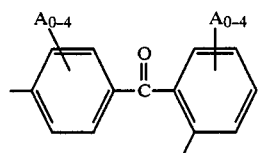

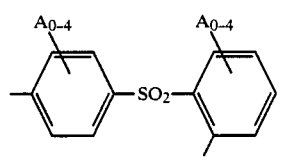

-continued

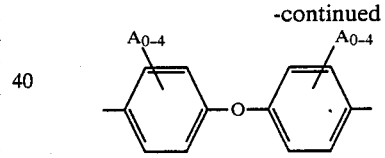

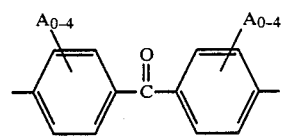

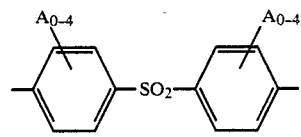

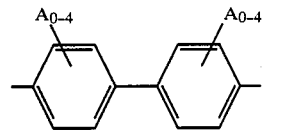

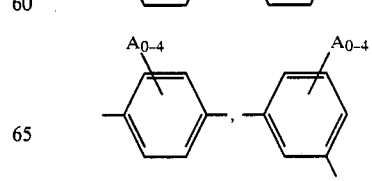

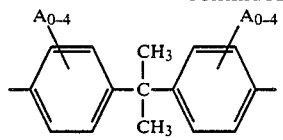

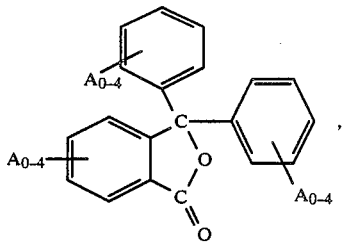,

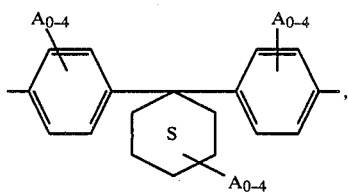,

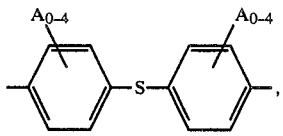, and isomers thereof, and wherein A is defined as above and X and Y are halogen or nitro, and particularly most preferably where W is selected from the following:

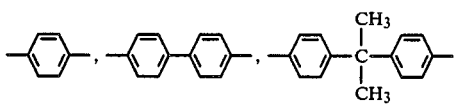,

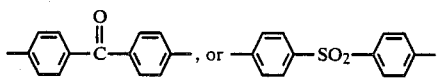

wherein A is hydrogen and X and Y are F or Cl.

(c) and one or more bisphenols HO—K'—OH where K' is selected from

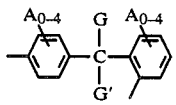

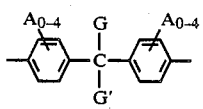

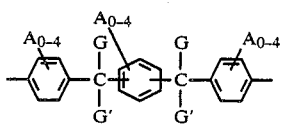

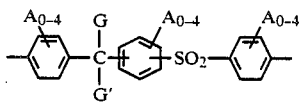

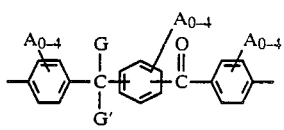

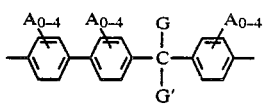

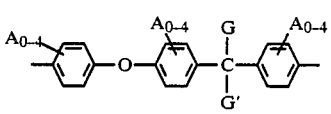

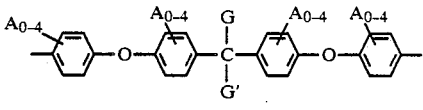

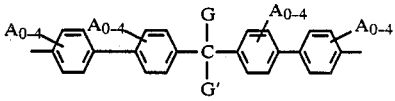

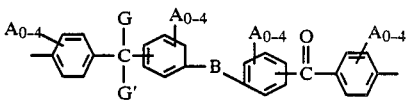

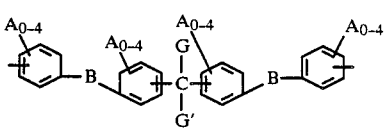

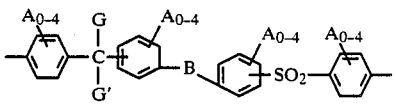

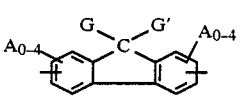

and isomers thereof, and wherein A and B are as defined above, and most preferably the following:

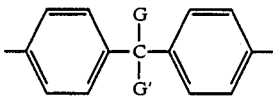

wherein A is hydrogen and G and G' are —OR, —SR, or —NR$_2$ wherein R is a substituted or unsubstituted alkyl, aryl, or aryl-alkyl of from 1 to about 20 carbon atoms and may contain heteroatoms or other non-interfering functional groups with the proviso that R should not contain functionality which is base sensitive such as hydroxyl, and G and G' may be the same or different and connected or unconnected; and most preferably G and G' are —OR.

Examples of R include methyl, ethyl, propyl, isopropyl, benzyl, cyclohexyl, and the like, and where G and G' are connected —CH$_2$CH$_2$—, —CH(CH$_3$)CH$_2$—, —CH(CH$_3$)CH(CH$_3$)—, —C(CH$_3$)$_2$CH$_2$—,

—C(CH₃)₂CH(CH₃)—, —C(CH₃)₂C(CH₃)₂—,
—CH₂CH₂CH₂, —CH₂C(CH₃)₂CH₂—,

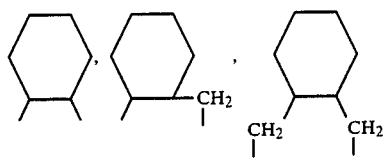

and the like.

The most preferred ketal bisphenol monomers are characterized as having formula (i) or (ii)

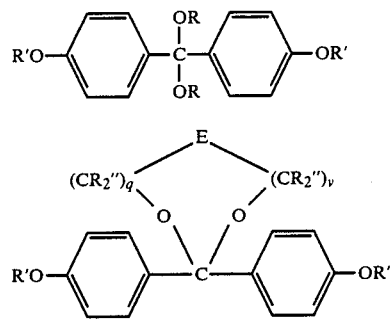

where R is as defined above, R' is hydrogen or —C(O)R''' wherein R''' is substituted or unsubstituted aryl or alkyl group containing 1 to about 20 carbon atoms, R'' is dependently selected from the group consisting of hydrogen, alkyl, aryl, arylalkyl containing from 1 to about 20 carbon atoms, substituted or unsubstituted, E is selected from the group consisting of a single bond, double bond, difunctional hydrocarbon, carbonyl, —O—, —S—, —SO—, —SO₂—, —NR—, and difunctional silicon, q is 1 or 2, and v is 1 or 2.

The most preferred ketal bisphenol monomers are of the following formula:

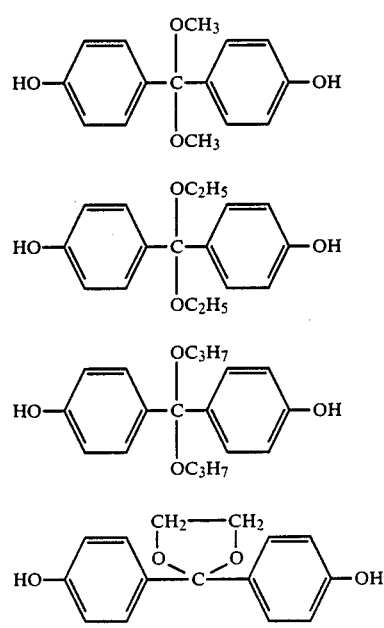

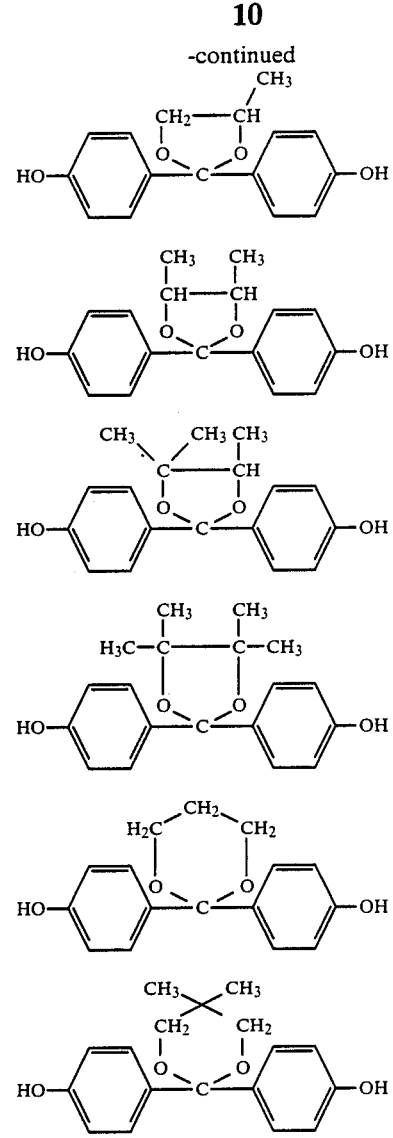

and their corresponding carboxylic acid esters.

Optionally, the polyketal may be derived from one or more of the monomers X-Z-Y, HO—W—OH, and HO—K'—OH or HO—L'—X wherein L' and X are as defined above wherein L' contains and unit —C(G)(G') wherein G and G' are defined above and G and G' are also combined and selected from the group consisting of =N—N—Ar, =NOH, =N—Ar' and =N—NH-CONR⁶R⁷, wherein Ar and Ar' are substituted or unsubstituted aryl of from about 5 to about 12 carbon atoms and R⁶ and R⁷ are hydrogen or as defined for R¹⁻⁵ above.

Preferred monomers HO—L'—X are those selected from the following

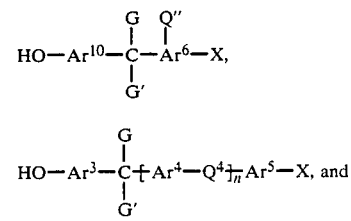

-continued

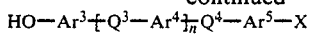

wherein Ar³⁻⁶, Ar¹⁰, Q″, G, and G′, are as defined above, Q⁴ is as defined above with the proviso that at least one Q⁴ is defined as for Q and Q′ and is ortho or para to X, Q³ is as defined above with the proviso that at least one Q³ is —C(G) (G′), and n is 1 to about 5, and wherein X is halogen or nitro.

Most preferably HO—L′—X is selected from the following:

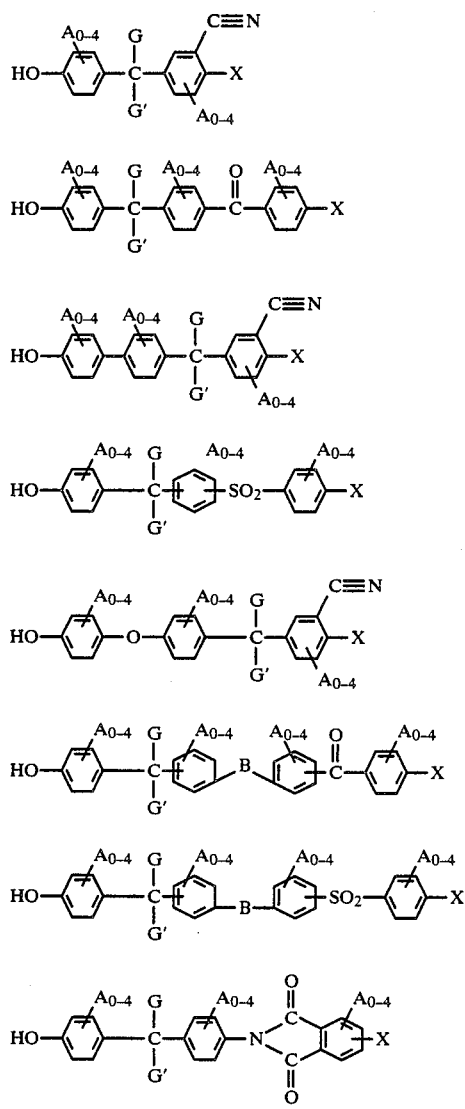

and isomers thereof, and wherein A and B are as defined above and X is F, Cl, or NO₂; G and G′ are —OR, —SR, or —NR₂ wherein R is a substituted or unsubstituted alkyl, aryl, arylalkyl of from 1 to about 20 carbon atoms and may contain heteroatoms or other non-interfering functional groups with the proviso that R not contain functionality which is base sensitive, such as hydroxyl, and G and G′ may be the same or different and connected or unconnected; and most preferably HO—L′—X is of the following formulae:

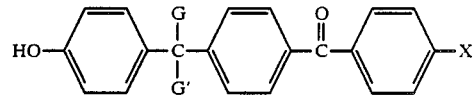

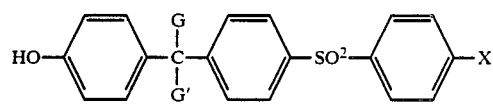

wherein A is hydrogen, X is F or Cl, and G and G′ are OR. Examples of ketal halophenol monomers include those of the following formulae:

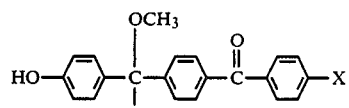

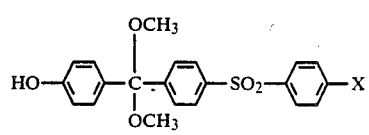

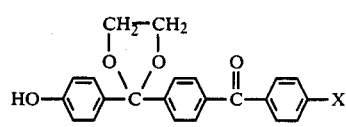

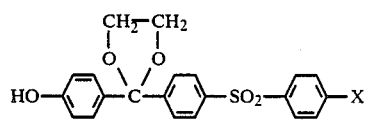

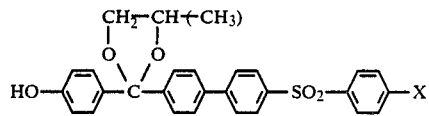

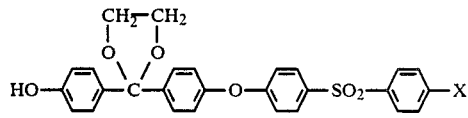

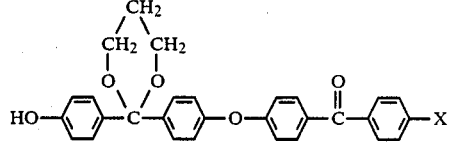

wherein X is F or Cl.

Also, the polyketal may optionally be derived from the halophenol monomer HO—L—X in combination with monomers HO—L′—X or HO—K′—OH, optionally HO—W—OH, and X-Z-Y where L and X are as defined above for L′ except that the group —C(G)(G′)— need not be present. Preferred halophenol monomers are the following:

where Ar³⁻⁵, Q³ and Q⁴ are as defined for HO—L′—X except that one or more Q³ need not be —C(G)(G′)— and n is 0 to 5.

Most preferred monomers include the following:

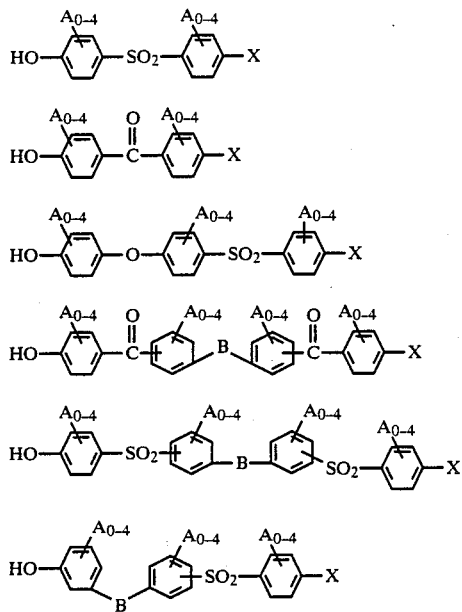

and isomers thereof and wherein A and B are as defined above and X is F, Cl, or nitro; especially preferred are the following:

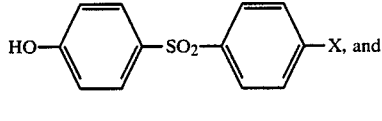

where A is hydrogen, and X is F or Cl

The polyketals are essentially linear polyethers comprised of the following repeat units:

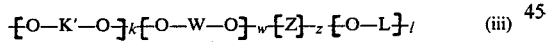 (iii)

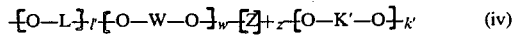 (iv)

where K', W, Z, L and L' are as defined above in their general, preferred, and most preferred embodiments and wherein k', w, z, l, and l' are the relative mole fractions selected so as to achieve the proper stoichiometric or near stoichiometric ratios for the desired oligomers and polymers. Thus it is obvious to one skilled in the art that the sum of k' and w must closely approximate z whereas the ratio of $z/l'$ or $z/l$ is not critical except that for the polyketals of this invention the mole fraction k' is greater than or equal to 0.01 in (iii) or mole fraction l' is greater than or equal to 0.01 in (iv).

Preferably, the mole fraction k' is greater than or equal to 0.1 in (iii) and l' is greater than or equal to 0.1 in (iv).

Polymers of this invention are generally amorphous when w and l are small in (iii), e.g., when both k' and z approximately equal 0.5 and both w and l approximately equal zero, or when w is small in (iv). It can be readily appreciated by one skilled in the art, however, that in those instances where k' and l' are zero or nearly zero, i.e., by not employing monomers HO—K'—OH or HO—L'—X, and the resulting polymer is crystalline, then the formation of high molecular weight is often more difficult to achieve due to crystallization of the polymer from the reaction medium. In such cases, it may be advantageous to use a sufficent proportion of HO—K'—OH or HO—L'—X so as to maintain polymer solubility in the reaction medium and, in so doing, reduce or eliminate the crystallinity of the polymer.

The most preferred polymers of this invention are those of the aforementioned most preferred monomers, i.e., polymers containing the following structural repeat units:

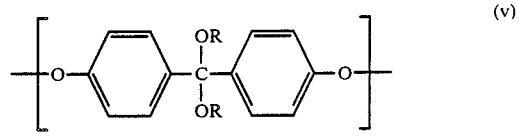 (v)

optionally with the following:

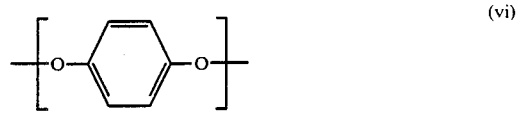 (vi)

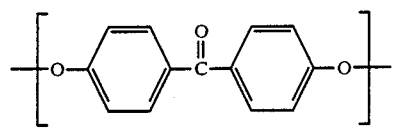

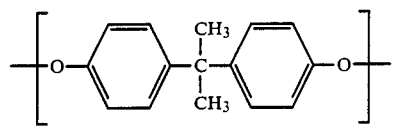

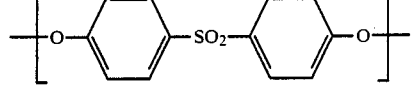

together with the appropriate molar equivalent proportion of the following:

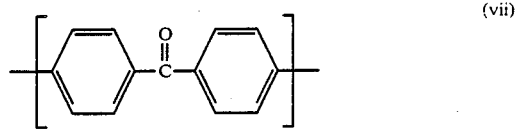 (vii)

and/or

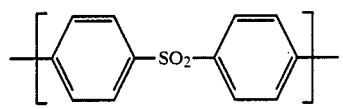

where R is as defined above.

The improved process for the preparation of the ketal monomers from the precursor diaromatic ketones containing at least one hydroxyl group ortho or para to the carbonyl comprises reacting the ketone precursor with a glycol in the presence of an alkylorthoester and a solid catalyst.

The precursor ketones are those analogous to the monomers HO—K'—OH and HO—L'—X described herein except that the group —C(G)(G') is replaced by a carbonyl and at least one hydroxyl group is situated ortho or para to said carbonyl.

The glycols, which include the heteroatom analogues such as thioglycols and dithiols, are of the general formula:

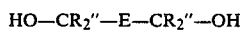

wherein R" and E are as defined above, preferably with E being a single bond, and which include ethylene glycol, propylene glycol, 2,3-butanediol, 2-methyl-1,2-propanediol, 2-methyl-2,3-butanediol, 2,3-dimethyl-2,3-butanediol, 1,3-propanediol, 2,2,-dimethyl-1,3-propanediol, and the like.

The alkylorthoesters include trimethyl orthoformate, triethyl orthoformate, trimethyl orthoacetate, triethyl orthoacetate, tetramethyl orthosilicate, tetraethyl orthosilicate, and the like. Readily hydrolyzed compounds such as 2,2-dimethoxypropane, 2,2-dimethyl-1,3-dioxolane, and the like, which form volatile products such as methanol, ethanol, acetone, and the like may be substituted for the orthoester.

The solid catalyst is preferably a finely divided acidic alumina-silica compound, and most preferably a montmorillonite clay as exemplified by the montmorillonite designated K-10 (obtained from United Catalysts). While the montmorillonite clays are preferred, other solid acidic catalysts with high surface areas may also function effectively as catalysts. These include acidic alumina, sulfonated polymer resins, as described in G. A. Olah et al, Synthesis, 282 (1981), and the like.

The reaction is conducted by simply mixing together the ketone precursor, about one equivalent or preferably an excess of the glycol, about one equivalent or preferably an excess of the orthoester, and at least 1 gram of the solid catalyst per equivalent of ketone, preferably 10 or more grams of solid catalyst per equivalent of ketone. The reaction is optionally conducted in the presence of an inert solvent. Since the catalyst is easily removed by filtration for reuse, large excesses of the solid may be conveniently employed.

The reaction is conducted at a temperature of from about 25° C. to about the boiling point of the orthoester used, but preferably at a temperature below the boiling point of the orthoester but above the boiling point of the orthoester reaction products. For example a reaction temperature of from about 65° C. to 95° C. is suitable when using trimethyl orthoformate (b.p. = 102° C.) the reaction products of which are methanol (b.p. = 65° C.) and methyl formate (b.p. = 34° C.). Of course, the reaction temperature can be adjusted appropriately when conducting the reaction under reduced or elevated pressures.

The most preferred ketal monomer is preferably prepared by heating a mixture of 4,4'-dihydroxybenzophenone, excess glycol, excess trialkyl orthoformate, and about 0.1 to about 5 gm montmorillonite clay per gram of ketone and preferably from about 0.5 to about 2.5 grams of clay per gram of ketone, so as to distill off the alcohol derived from the orthoformate. The ketal, 2,2-bis(4-hydroxyphenyl)-1,3-dioxolane, can be obtained in excellent yield (60% to almost quantitative) in less than 48 hours reaction time.

Standard isolation methods can be employed to recover the ketal monomer and unreacted ketone, if any, with due care to avoid acidic aqueous environments. In some cases recrystallization or other extensive purification of the isolated reaction product may be unnecessary prior to use in the process to prepare a polyketal. Thus, for example, after dilution of the reaction with ethyl acetate solvent, filtration to remove the solid catalyst, extraction of the solution with basic water to remove excess glycol, drying with a conventional drying agent such as anhydrous sodium sulfate, removal of the solvent and volatile materials under vacuum, and then washing the resulting solid with a solvent such as methylene chloride to remove minor contaminants, a reaction product is obtained which contains primarily ketal bisphenol monomer but may still contain some unreacted ketone precursor. This reaction product may be used without further purification to prepare high molecular weight polyketal.

In general the reaction conditions employed to prepare the polyketals are those used for effecting polymerization of bisphenols with bishalobenzenoid compounds or of halophenols for the preparation of polyarylethers.

The preparation of the polyketals is conducted in the presence of a base in a dipolar aprotic solvent, and preferably in the presence of an inert azeotropic agent, at temperatures above about 100° C.

The base which may be used is one capable of reacting with the aromatic hydroxyls of the bisphenol or halophenol monomers to form the mono or disalts thereof. Alkali metal carbonates, bicarbonates, hydroxides, and mixtures thereof, are commonly used in near stoichiometric amounts or in excess. Although the mono or disalts can often be formed separately and isolated for the polymerization reaction, it is usually preferable to react the hydroxyl monomers with the base in situ either prior to addition of the bishalobenzenoid monomer or during the polymerization step in the presence of the bishalobenzenoid monomer. In the latter case the alkali metal carbonates and mixtures thereof are particularly useful.

The dipolar aprotic solvents commonly used include dialkylamides such as dimethylformamide and dimethylacetamide; cyclicalkylamides such as N-methylpyrrolidinone and N-propylpyrrolidinone, acyclic and cyclic ureas such as N,N'-dimethylpropleneurea and 1,2-dimethyl-2-imidazolidinone; dialkyl and diaryl sulfoxides such as dimethyl sulfoxide; dialkyl, diaryl, and cyclic sulfones such as dimethyl sulfone, diphenyl sulfone, and sulfolane; sulfamides and phosphoramides, such as N,N,N,N'-tetraethyl sulfamide and hexamethyl phosphoramide, and the like. Generally, the lower boiling solvents (b.p. < 290° C.) are preferred.

The azeotropic agent used to remove the water of reaction or water introduced into the reaction is generally any inert compound which does not substantially interfere with the polymerization, codistills with water, and boils between about 25° and about 250° C. Common azeotropic agents include benzene, toluene, xylene, chlorobenzene, methylene chloride, dichlorobenzene, trichloro-benzene, and the like. It is advantageous, of course, to select the azeotropic agent such that its boiling point is less than that of the dipolar solvent used. Although an azeotropic agent is commonly used, it is not always necessary when higher reaction temperatures, for example, above 200° C., are employed especially when the reaction mixture is continuously sparged with inert gas.

It is generally desirable to conduct the reaction in the absence of oxygen under an inert atmosphere.

The reaction can be carried out at atmospheric, subatmospheric, or superatmospheric pressures.

Other catalysts, salts, diluents, processing aids, additives, and the like may also be present or added during the reaction provided they do not substantially interfere with the polymerization reaction, either directly or indirectly.

Reaction temperatures of up to about 250° C. are generally sufficient for the polymerization reaction although higher temperatures can be used if necessary. The temperature will depend, of course, on the solvent boiling point and the reaction pressure and will also affect the reaction rate. In general, under atmospheric conditions, the reaction temperature will be from about 100° C. to about 165° C. in dimethylacetamide; to about 240° C. in sulfolane; and to about 200° C. in N-methylpyrrolidinone.

Obviously, the reaction solvent, the base, and the reaction temperature should be selected so as to obtain a reasonable polymerization rate and also to avoid degradation of the solvent, monomers or polymers which may cause interference with the polymerization. It is also preferable, of course, to select the reaction solvent and reaction temperature so as to maintain the growing polymer chain in solution.

Once the desired polymer molecular weight is achieved, the phenate end groups can optionally be reacted by introducing an end-capping reagent, such as methyl chloride to form the stable methyl ether end group, or alternatively, reagents to form other reactive or stable end groups, as desired.

The preferred reaction conditions using the preferred monomers involves reacting, under argon or nitrogen atmosphere, essentially stoichiometric amounts of the monomers in the presence of from about 1 to about 50 percent excess of dried potassium carbonate in dimethylacetamide (or sulfolane) with toluene (or chlorobenzene) azeotrope at about 115° C. (or 160° C.) initially under reflux of the azeotropic solvent, gradually increasing the reaction temperature from about 155° to about 165° C. (or from about 180° to about 220° C.) by allowing some toluene (or chlorobenzene) to distill. The reaction is held at this temperature until the desired molecular weight polymer is formed, usually in about 0.5 to about 8 hours. The reaction is diluted with dimethylacetamide (or sulfolane or other solvent) cooled to about 100° to about 150° C. Methyl chloride is then sparged through the reaction mixture for about 0.2 to about 2 hours to end-cap the polymer.

Commonly practiced polymer recovery methods can be used, such as coagulation into water or an organic (non)solvent; the recovered polymer is optionally washed with water and alcohol or other solvents and dried. Other recovery methods such as extraction, filtration, devolatilization, and the like, may also be used.

EXAMPLES

The following examples serve to give specific illustrations of the practice of this invention but they are not intended in any way to limit the scope of this inventions.

The reduced viscosity (RV) of the polymer was measured in concentrated sulfuric acid at 25° C. (1 gm of polymer dissolved in 100 ml of concentrated sulfuric acid). The calculation of the RV is based on the original polymer sample weight, regardless of any chemical reaction which may take place in the sulfuric acid solution. Therefore, the RVs are regarded as the RV in concentrated sulfuric acid solution (1 gm/100 ml solution) and not necessarily as the RV of the polymer itself.

EXAMPLE 1

Preparation of Dimethylketal Bisphenol [bis(4-hydroxyphenyl)dimethoxymethane]

A reaction flask was charged with 11.0 grams (gm) of 4,4'-dihydroxybenzophenone (97 percent, 50 mmole), 6.5 gm of trimethylorthoformate (TMOF, 98 percent, 60 mmole), 75 ml methanol and 1 drop of concentrated aqueous hydrogen bromide and heated in an oil bath (100° to 106° C.) with a reflux head set for very slow takeoff. After about 18 hours approximately 50 ml of material had distilled over; an additional 5 gm of TMOF, 50 ml of methanol, and one drop of hydrogen bromide was added and the reaction continued for another 6.5 hours with slow distillation. TMOF (4 gm), 25 ml of methanol, and one drop of hydrogen bromide were added and the reaction continued for 16 hours under total reflux. An additional 3 gm of TMOF and 15 ml of methanol was added and heating resumed with maximum takeoff for 7.5 hours by which time most of the methanol had distilled out. The reaction was cooled and neutralized with sodium acetate.

The residual solvent was removed under vacuum and the resulting orange residue was slurried in 200 ml of methylene chloride with 0.1 gm sodium carbonate. The slurry was filtered and the solid retreated with 200 ml of methylene chloride and refiltered. The combined methylene chloride solutions were evaporated to give 6.1 gm isolated product (after drying at 0.1 mm). NMR analysis showed 90 percent of the ketal; an $A^2B^2$ quartet centered at 7.35 ppm (aromatic, 8H) and singlet at 3.20 ppm (methyls, 6H). Overall yield was 47 percent (correcting for purity).

The ketal was converted to its diacetate by reaction with acetic anhydride in pyridine (91 percent isolated yield). NMR of the diacetate showed the expected transitions; an $A^2B^2$ quartet at 7.23 ppm (aromatic, 8H), singlet at 3.07 ppm (—OCH$_3$, 6H), and singlet at 2.20 ppm (CH$_3$CO—, 6H).

EXAMPLE 2

2,2-bis(4-hydroxyphenyl)-1,3-dioxolane Azeotrope Method

A 250 ml flask fitted with a magnetic stir bar, Dean-Stark trap, condenser, and drying tube was charged with 10 gm of 4,4'-dihydroxybenzophenone (46.7 mmoles), 16 gm of ethylene glycol (dried over molecular sieves, 258 mmole), 100 ml of benzene, and 2 drops of concentrated aqueous hydrogen bromide and heated to reflux. After 4 days reflux, the trap was drained and charged with freshly dried molecular sieves and fresh benzene, and reflux resumed. The molecular sieves in the trap were replaced with fresh sieves three times over the ensuing 13 days; in addition 2 more drops of hydrogen bromide and 100 ml of benzene were added during this time. Most of the benzene was distilled off and the reaction mixture dissolved in ethyl acetate, washed 4 times with 5% sodium bicarbonate solution, washed with sodium chloride solution and dried over sodium sulfate. The solvent was removed by evaporation under vacuum (final drying at 0.2 mm pressure) to give crude product; NMR analysis showed a mixture of ketal and starting ketone. The crude material was slurried in 500 ml of methylene chloride, filtered and the methylene chloride solution evaporated to give essentially pure ketal; 3.7 gm (30.7% yield.) NMR spectrum of the ketal is consistent with the structure: $A^2B^2$ quartet centered at 7.45 ppm (aromatic, 8H), singlet at 4.07 ppm (—$OCH_2$—, 4H).

The diacetate of the ketal bisphenol was prepared by reaction with acetic anhydride in pyridine (75% yield). The NMR spectrum is also consistent: $A^2B^2$ quartet centered at 7.42 ppm (aromatic, 8H); singlet at 3.88 ppm (—O—$CH_2$—, 4H); and a singlet at 2.17 ppm ($CH_3CO$—, 6H). The melting point of diacetate was 118°–121° C.

Elemental analysis of the ketal bisphenol gave 69.83% C, 5.59% H, 24.69% O; calculated 69.76% C, 5.46% H, and 24.78% O.

The preparation of 2,2-diphenyl-1,3-dioxolane from benzopheone under similar conditions is reported to give over 80% yield in only 5 hours reaction time, [M. Sulzbacher et al., J. Amer. Chem. Soc., 70, 2827 (1948)]. It is readily apparent that the synthesis of the ketal of 4,4'-dihydroxybenzophenone is accomplished less advantageously than the corresponding ketal of benzophenone.

EXAMPLE 3

2,2-bis(4-hydroxyphenyl)-1,3-dioxolane

The procedure of Example 2 was repeated employing a very large excess of glycol and a much higher proportion of acid catalyst. Thus, 25 mmole of ketone, 625 mmole of ethylene glycol, and 2.5 mmole of hydrogen bromide were reacted under benzene azeotrope (80° C.); after an extended reaction time, i.e. 5 days, NMR analysis of the reaction mixture showed 80% conversion of the ketone to the desired ketal.

EXAMPLE 4

2,2-bis(4-hydroxyphenyl)-4-methyl-1,3-dioxolane

Azeotrope Method

The procedure of Example 3 was repeated replacing the ethylene glycol with propylene glycol and the benzene with toluene. Thus, 50 mmole of ketone, 1250 mmole of propylene glycol [1,2-propanediol], and 2.4 mmole of hydrogen bromide catalyst were heated under toluene reflux (113° C.); after 4 days reaction time, NMR analysis of the reaction mixture showed 90% conversion of the desired ketal.

EXAMPLE 5

2,2-bis(4-hydroxyphenyl)-1,3-dioxolane

Clay/Orthoformate Method

A one-liter flask fitted with a mechanical stirrer, jacketed condenser, and a variable take-off distillation head was charged with 66 gm of 4,4'-dihydroxybenzophenone (97%, 0.30 mmole), 186 gm of ethylene glycol (3 moles), 96 gm of trimethylorthoformate (0.9 mole), and 150 gm acidic montmorillonite clay (K-10, United Catalysts). The reaction mixture was stirred and heated in an oil bath (75° to 80° C.) for 18 hours while distilling over methylformate and methanol. An additional 96 gm of trimethylorthoformate was added and heating continued for 25 hours. A sample was taken from the reactor and NMR analysis showed 82% conversion to ketal. An additional 36 gm of trimethylorthoformate was added and the reaction heated in a bath (100° to 110° C.) until distillation had essentially stopped.

The reaction was cooled, diluted with ethyl acetate, filtered to remove the clay, and the clay washed with ethyl acetate. The organic solution was washed four times with 2% solution of sodium bicarbonate, once with saturated sodium chloride, solution, dried over sodium sulfate, filtered, and the solvent removed under vacuum. The crude product was slurried with 200 ml of methylene chloride, filtered, and dried to give 57.6 gm of product. Gas chromatographic analysis of the acetylated product (acetic anhydride, pyridine) showed it to contain 86.6% of the desired ketal and 13.4% starting 4,4'-dihydroxybenzophenone. The conversion based on isolated product was 64.8%; the total isolated yield was 76.9% including recovered ketone. Compared to Examples 2 and 3 high yields are obtained in significantly shorter reaction times.

EXAMPLE 6

The procedure of Example 5 was repeated using triethylorthoformate instead of trimethylorthoformate and at higher reaction temperature. Thus, 10 mmoles of ketone, 50 mmoles of ethylene glycol and 30 mmoles of triethylorthoformate in the presence of 1 gm of montmorillonite clay were reacted at 120° C. for 24 hours. Isolation of the reaction product gave 2.48 gm which was shown to be 77.4% pure by gpc; the calculated conversion to ketal was 74%. Thus, high yield was obtained.

EXAMPLE 7

The procedure of Example 5 was repeated except that azeotropic reflux with benzene was used instead of the orthoformate. Thus 75 mmoles of ketone, 750 mmoles of ethylene glycol, and 15 gm of montmorillonite clay were refluxed with 75 ml of benzene at 80° C. using a Dean-Stark trap to collect the water distilled over; after 47 hours the reaction was worked up yielding 14.3 gm crude product NMR analysis of which showed 25 mole % ketal (18% conversion). This example illustrates that the clay catalyst does not effect efficient formation of the ketal when benzene azeotrope instead of orthoester is used to remove the water of reaction.

EXAMPLE 8

The procedure of Example 5 was repeated except that hydrogen bromide catalyst was used instead of the clay. Thus, 60 mmoles of ketone, 340 mmoles of ethylene glycol, and a total of 170 mmoles of trimethylorthoformate added in portions were reacted in the presence of 3 drops concentrated hydrogen bromide at 85° C. for a total of 120 hours; toward the end of this period the reaction temperature was raised to 120° C. to distill off the excess unreacted orthoformate; work up of the reaction yielded 13.1 gm of product which was shown to contain about 21 mole % ketal by NMR (calculated conversion 17.8%). A similar experiment using hydrogen bromide and p-toluenesulfonic acids together in place of the clay gave an isolated product containing only 36 mmole % ketal after 120 hours at 70°–95° C.

This example illustrates that using strong acid catalyst in place of the clay does not effect efficient conversion to the ketal even when orthoester is present.

EXAMPLE 9

Preparation of Polyketal

A 500 ml 4-neck reaction flask fitted with a mechanical stirrer, thermometer, argon inlet, jacketed Vigreaux column, Dean-Stark trap and condenser was charged with 23.16 gm of 2,2-bis(4-hydroxyphenyl)-1,3-dioxolane (97.95 percent ketal and 2.05 percent of 4,4'-dihydroxybenzophenone by vpc analysis, 90.03 mmoles total monomers), 19.64 gm of 4,4'-difluorobenzophenone (90.03 mmole), 160 ml of dried dimethylacetamide, 115 ml of toluene, and 18.68 gm of dried, anhydrous potassium carbonate. The reaction mixture was stirred and purged with argon for one hour, heated to reflux in an oil bath, and the reflux temperature was gradually increased from 119° to 150° C. by removing distillate from the trap and adding small amounts of toluene to the reaction flask. After about 5.5 hours, a solution of 0.02 gm of 4,4'-difluorobenzophenone in 2 ml of dimethylacetamide was added to the viscous reaction mixture to assure stoichiometry. After an additional 30 minutes, the heating bath was removed and 135 ml dimethylacetamide added to dilute the reaction.

The reaction temperature was then adjusted to 110° C. and methyl chloride gas was bubbled through the reaction mixture for about one hour (using the argon inlet tube) to end-cap the phenate end-groups, during which the yellow-green reaction mixture changed to a creamy beige color. The reaction mixture was then heated to 150° C. and filtered through a sintered glass funnel. The filtrate was coagulated into excess isopropanol and the polymer washed with isopropanol, distilled water, and methanol and dried under vacuum at 100° C. to give 35.5 gm of polymer (89.8 percent isolated yield). The RV of the polymer was 0.80 in chloroform (0.2 percent, 25° C.) and 1.64 in concentrated sulfuric acid (1 percent, 25° C.).

The polymer was molded at 250° C. to give a clear, tough plaque with excellent color with the following mechanical properties:

| | |
|---|---|
| Tensile modulus (ASTM D-638) | 280,000 psi |
| Tensile strength (ASTM D-638) | 9,520 psi |
| Yield strength (ASTM D-638) | 8,800 psi |
| Yield elongation (ASTM D-638) | 5.0% |
| Elongation at break (ASTM D-638) | 115% |
| Pendulum impact strength - (ASTM D-256) | >250 ft-lbs/in$^3$ |
| Glass transition temperature | 155° C. |

The polymer was amorphous, i.e., exhibited no melting transition by differential scanning calorimetry.

EXAMPLE 10

Preparation of Polyketal

The reaction of 2,2-bis(4-hydroxyphenyl)-1,3-dioxolane (4.655 gm, 18.03 mmoles), 4,4'-dihydroxybenzophenone (0.429 gm, 2.00 mmole) and 4,4'-difluorobenzophenone (4.370 gm, 20.03 mmole) was conducted by the procedure of Example 9 except on a smaller scale (4.15 gm potassium carbonate, 35 ml dimethylacetamide, 25 ml toluene charged) to give polyketal polymer with an RV equal to 1.37 (1 percent in sulfuric acid at 25° C.).

This example shows that 4,4'-dihydroxybenzophenone can be substituted for at least 10 mole percent of the ketone monomer and high molecular weight polymer produced.

EXAMPLE 11

Polyketal was prepared by the procedure of Example 10 except that the bisphenol monomer mixture was the reaction product prepared and isolated essentially as described in Example 5. Thus, the reaction was charged with 25.2235 gm of 2,2-bis(4-hydroxyphenyl)-1,3-dioxolane reaction product containing 13.72% unreacted 4,4'-dihydroxybenzophenone by gpc analysis (0.1 mole total bisphenols by gpc analysis), 22.1473 gm of 4,4'-difluorobenzophenone (0.1015 mole), 125 ml of dimethylacetamide, 125 ml of toluene and 20.75 gm of potassium carbonate. The polymerization was conducted as in Example 9; after 5 hours at 150° to 160° C., the polymer was end-capped with methyl chloride and recovered by coagulation yielding 37.6 gm. of polymer with an RV=1.17 (one percent in concentrated sulfuric acid, 25° C.).

This example illustrates that high molecular weight polyketal polymer was prepared using the isolated reaction product obtained from the improved ketal process as in Example 5 without requiring extensive monomer purification such as recrystallization.

EXAMPLE 12

2,2-bis(4-hydroxyphenyl)-1,3-dioxolane was prepared by the procedure of Example 5 by mixing together, in a reaction flask fitted with a mechanical stirrer, thermometer, and variable take-off distillation head, 99 gm of 4,4'-dihydroxybenzophenone (97% pure, 0.448 mole), 269 gm of ethylene glycol (4.3 moles), 96 gm of trimethyl orthoformate (0.91 mole), and 150 gm of montmorillonite clay (K-10, United Catalysts) and heating the reaction mixture at 70° to 90° to give slow distillation of the reaction by-products. After about 18 hours, 66 gm of distillate had been collected, an additional 64 gm of trimethylorthoformate (0.60 mole) was added to the reaction mixture, and the reaction continued. After a total of 24 hours reaction time, NMR analysis of a reaction sample showed about 2.23 mole ratio of ketal product to ketone starting material; after a total of 48 hours reaction time, NMR analysis of a second reaction sample showed the mole ratio was about 19 (about 95% conversion to ketal product). The reaction mixture was heated for an additional 8 hours and then cooled; NMR analysis again showed about 95% conversion.

The reaction mixture was worked up as in Example 5 by dilution with ethyl acetate, filtration to remove the clay, extraction with basic water to remove glycol, drying over anhydrous sodium sulfate, and removal of solvent to give 115 gm of crude product which was then ground, stirred twice with methylene chloride, filtered, and the solid dried under vacuum to give 99.9 gm of creamy white product. Gas chromatographic analysis of the derivatized diacetate product (acetic anhydride, pyridine) showed it to contain 95.4 wt % ketal and 4.6% ketone. The isolated yield of ketal was 82.5% (87.2% yield including recovered ketone).

This example further illustrates that the improved process of this invention affords as much as 95% conversion to 2,2-bis(4-hydroxyphenyl)-1,3-dioxolane within 48 hours and excellent isolated yields of this ketal bisphenol can be obtained.

What is claimed is:

1. A compound of the formula:

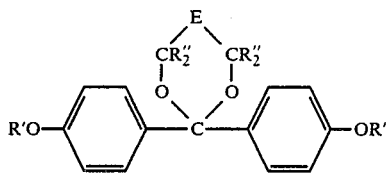

wherein R' is hydrogen or —C(O)R''', wherein R''' is aryl or an alkyl group containing from 1 to about 20 carbon atoms, R" is independently selected from the group consisting of hydrogen, alkyl, aryl, arylalkyl containing up to about 20 carbon atoms, E is selected from the group consisting of a single bond and a double bond.

2. A compound of the formula:

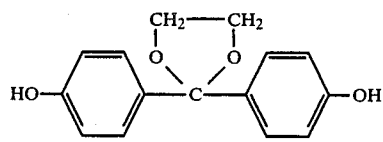

or the carboxylic acid esters thereof.

3. A compound of the fomrula:

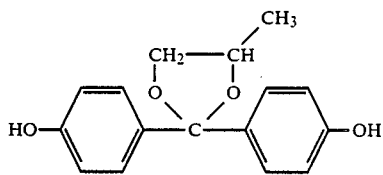

or the carboxylic acid esters thereof.

4. A compound of the formula:

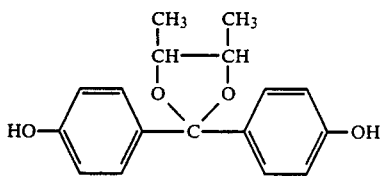

or the carboxylic acid esters thereof.

5. A compound of the formula:

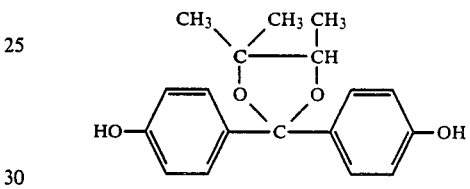

or the carboxylic acid esters thereof.

6. A compound of the formula:

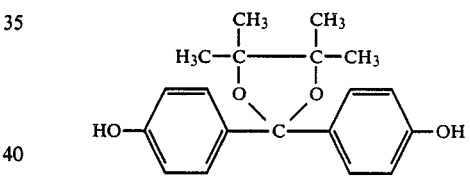

or the carboxylic acid esters thereof.

* * * * *

UNITED STATES PATENT OFFICE
CERTIFICATE OF CORRECTION

Patent No. 4,774,344  Dated September 27, 1988

Inventor(s) Kelsey

It is certified that error appears in the above-identified patent and that said Letters Patent is hereby corrected as shown below:

PATENT

| Column | Line | |
|---|---|---|
| 2 | 65 | "ortho of para" should read --ortho or para-- |
| 9 | 34 | "dependently" should read --independently-- |
| 10 | 48 | "contains and unit" should read --contains the unit-- |
| 16 | 47 | "N,N'-dimethylpropleneurea" should read --N,N'-dimethylpropyleneurea-- |
| 16 | 52 | "N,N,N,N'-tetraethyl" should read --N,N,N',N'-tetraethyl-- |
| 19 | 19 | "benzopheone" should read --benzophenone-- |
| 19 | 50 | "of" should read --to-- |
| 21 | 7 | "(4-hydroxphenyl)" should read --(4-hydroxyphenyl)-- |
| 13 | 47 | "$\{O-L\}_l, \{O-W-O\}_w\{Z\}_z\{O-K'-O\}_{k'}$ (iv)" to read -- $\{O-L\}_l, \{O-W-O\}_w\{Z\}_z\{O-K'-O\}_{k'}$ (iv) --. |

Signed and Sealed this

Ninth Day of May, 1989

Attest:

DONALD J. QUIGG

Attesting Officer    Commissioner of Patents and Trademarks